(12) United States Patent
Li et al.

(10) Patent No.: US 6,872,361 B2
(45) Date of Patent: Mar. 29, 2005

(54) DUAL PAD LIQUID SHEAR VALVE ASSEMBLY

(75) Inventors: William Weigong Li, Miami, FL (US); Helen A. Minnich, Davie, FL (US)

(73) Assignee: Coulter International Corp., Miami, FL (US)

( * ) Notice: Subject to any disclaimer, the term of this patent is extended or adjusted under 35 U.S.C. 154(b) by 574 days.

(21) Appl. No.: 09/894,795

(22) Filed: Jun. 28, 2001

(65) Prior Publication Data

US 2003/0026741 A1 Feb. 6, 2003

(51) Int. Cl.$^7$ .............................. F16K 3/00; B01L 11/00
(52) U.S. Cl. ................. 422/103; 73/863.73; 251/149.1; 251/143
(58) Field of Search ....................... 422/103; 73/863.73; 251/149, 149.1, 142, 143, 153

(56) References Cited

U.S. PATENT DOCUMENTS

| | | | |
|---|---|---|---|
| 3,567,389 A | | 3/1971 | Coulter et al. |
| 4,445,391 A | | 5/1984 | Cabrera |
| 4,507,977 A | | 4/1985 | Cabrera |
| 4,577,515 A | * | 3/1986 | Someya et al. .......... 73/863.73 |
| 4,702,889 A | | 10/1987 | Cabrera et al. |
| 4,726,237 A | * | 2/1988 | Yung ...................... 73/864.83 |
| 4,729,876 A | * | 3/1988 | Hennessy et al. ........... 422/103 |
| 4,822,569 A | | 4/1989 | Pellegrino |
| 4,896,546 A | | 1/1990 | Cabrera et al. |
| 4,957,008 A | | 9/1990 | Proni et al. |
| 5,158,751 A | | 10/1992 | del Valle et al. |
| 5,255,568 A | | 10/1993 | del Valle et al. |
| 5,390,552 A | * | 2/1995 | Demachi et al. ......... 73/863.73 |
| 5,542,305 A | | 8/1996 | Hollinger |
| 5,650,577 A | * | 7/1997 | Nagai et al. ............. 73/863.73 |
| 5,691,486 A | | 11/1997 | Behringer et al. |
| 6,322,752 B1 | | 11/2001 | Siddiqui et al. |

* cited by examiner

Primary Examiner—Jan M. Ludlow
(74) Attorney, Agent, or Firm—Warren W. Kurz; Mitchell E. Alter

(57) ABSTRACT

A shear valve assembly comprises a pair of valve pads having opposing planar surfaces supported for relative sliding engagement. Each valve pad defines a plurality of liquid pathways by which a liquid can be passed from one pad to the other. The planar surface of one of the valve pads has an open channel formed therein, such channel having dimensions to accommodate a prescribed volume of liquid. Liquid is introduced into such channel via a first pair of pathways formed in the other valve pad, and liquid is dispensed from the open channel by a second pair of pathways that are brought into alignment with the channel during sliding movement between the valve pads. The valve assembly is particularly useful in blood-analyzing instruments for isolating and dispensing relatively minute volumes (of the order of microliters) of whole blood for analysis.

18 Claims, 5 Drawing Sheets

DUAL PAD LIQUID SHEAR VALVE ASSEMBLY

FIELD OF THE INVENTION

The present invention relates in general to improvements in shear valve assemblies for isolating precise volumes of liquid for subsequent delivery to a utilization device or instrument. The apparatus of the invention is particularly useful in blood analyzing instruments, such as hematology instruments and flow cytometers, for isolating relatively minute volumes (of the order of microliters) of blood for analysis.

BACKGROUND OF THE INVENTION

In automated blood-analyzing instruments, such as hematology instruments and fluorescent flow cytometers, it is necessary to mix precisely measured minute volumes, typically of the order of between 5 and 50 microliters, of patient blood with diluents and/or reagents in order to prepare blood samples for analysis. To do this, it is necessary to isolate small volumes of a blood sample aspirated from a vial of blood and to position these isolated volumes so that they may be readily dispensed into different mixing chambers. There are a number of liquid-metering shear valves that are capable of providing these functions; see, e.g., the blood-sampling shear valve assemblies disclosed in the respective disclosures of U.S. Patents to: Coulter et al, U.S. Pat. No. 3,567,389; Cabrera, U.S. Pat. Nos. 4,445,391 and 4,507,977; Cabrera et al., U.S. Pat. Nos. 4,896,546 and 4,702,889; Pellegrino, U.S. Pat. No. 4,822,569; Proni et al., U.S. Pat. No. 4,957,008; Del Valle et al., U.S. Pat. Nos. 5,158,751 and 5,255,568; and Hollinger, U.S. Pat. No. 5,542,305.

All of the shear valve assemblies disclosed in the above patents comprise a stacked set of three disc-shaped pads having confronting planar surfaces. These pads, each being made of ceramic material, are arranged on a common axis about which at least the middle pad of the set is rotatably mounted. The middle pad defines a cylindrically-shaped "segmenting passageway" that extends axially through the entire width of the pad, i.e., between its opposing planar and parallel surfaces. Thus, the volume of this segmenting passageway is determined by the product of its diameter and the thickness of the middle pad. In use, this passageway is used to isolate one of at least two of the required prescribed volumes of blood needed for analysis in a conventional hematology instrument. A second, and somewhat larger, prescribed volume of blood needed for analysis is provided by a hollow external loop that is fluidly connected in series with the segmenting passageway. Thus, a blood sample entering the valve assembly through a port formed in one of the end pads will fill both the segmenting passageway and the hollow external loop, one after the other. As the middle pad is rotated relative to the end pads from a "blood-loading" position, in which blood can enter and fill the two prescribed volumes, and towards a "blood-dispensing" position, in which the two prescribed volumes can be dispensed, the blood flow entering the assembly is sheared off, and the two prescribed blood volumes contained respectively in the segmenting passageway and the external hollow loop are isolated from each other, as well as from the rest of the blood within the valve assembly. Continued rotation of the middle pad towards its blood-dispensing position operates to align the segmenting passageway and the external hollow loop with different ports formed in the respective end pads, thereby enabling the isolated blood volumes to be dispensed to a mixing station or elsewhere. When so aligned, a diluent or reagent that is to be ultimately mixed with the isolated blood sample is used to drive the sample from isolation, such diluent or reagent entering the assembly under pressure through a port in one of the end pads, engaging the isolated sample, and expelling the sample out of the assembly through a port formed in the opposite end pad.

From the above description, it will be appreciated that the shear valve assemblies of the type disclosed in the above patents require at least three valve pads in order to extract or dispense the blood contained in the segmenting passageway. This requirement, of course, adds significant cost and complexity to the valve assembly and can adversely affect its reliability.

SUMMARY OF THE INVENTION

In accordance with the invention, the above-noted shortcomings of the conventional three-pad shear valve architecture described above are effectively obviated by a more compact valve architecture comprising only two valve pads having confronting planar surfaces. According to the invention, a planar surface of one of the valve pads defines an open, liquid-retention channel that is arranged to be brought into and out of alignment with liquid ports formed in the other valve pad as the two valve pads and their respective planar surfaces are slidably moved relative to each other between a liquid-loading position and a liquid-dispensing position. This valve pad configuration enables a prescribed volume of liquid, supplied via liquid ports formed in the other valve pad, to be captured and isolated in the open liquid-retention channel for subsequent delivery to additional liquid-dispense ports of the other pad as a result of said relative movement between the pads. Preferably, the other pad supports an external hollow loop of prescribed volume that is in series communication with the open, liquid-retention channel when the valve pads are in their respective liquid-loading positions. When the valve pads move to their liquid-dispensing positions, the external hollow loop and the open, liquid-retention channel are isolated from each other and the source of liquid, but they are now aligned with liquid-dispensing ports formed in the opposing valve pads. At the same time, the liquid-loading ports formed in each valve pad and through which liquid was previously loaded into the valve assembly are aligned with rinse ports formed in the opposing valve pads, whereby the liquid-load ports may be cleansed during liquid dispensing.

Pursuant to a non-limiting embodiment of the invention, one of the valve pads is fixed, while the other pad is supported for linear, slidable translation along the one pad within a reduced volume housing. The fixed valve pad contains a plurality of liquid ports, two of which are arranged to become aligned with the above-noted open liquid-retention channel formed in the planar surface of the movable valve pad. Preferably, two of these two liquid ports are ported to the above-noted external hollow loop section. In addition, the fixed valve pad is provided with a cleaning groove ported to a vacuum source.

According to another aspect of the invention, the valve assembly of the invention is contained in a specialized housing adapted to maintain the necessary relationship between the valve pads during relative movement thereof.

The invention and its advantages will be better understood from the ensuing detailed description of preferred embodiments, reference being made to the accompanying drawings in which like reference characters denote like parts.

DETAILED DESCRIPTION OF PREFERRED EMBODIMENTS

Figure 1:
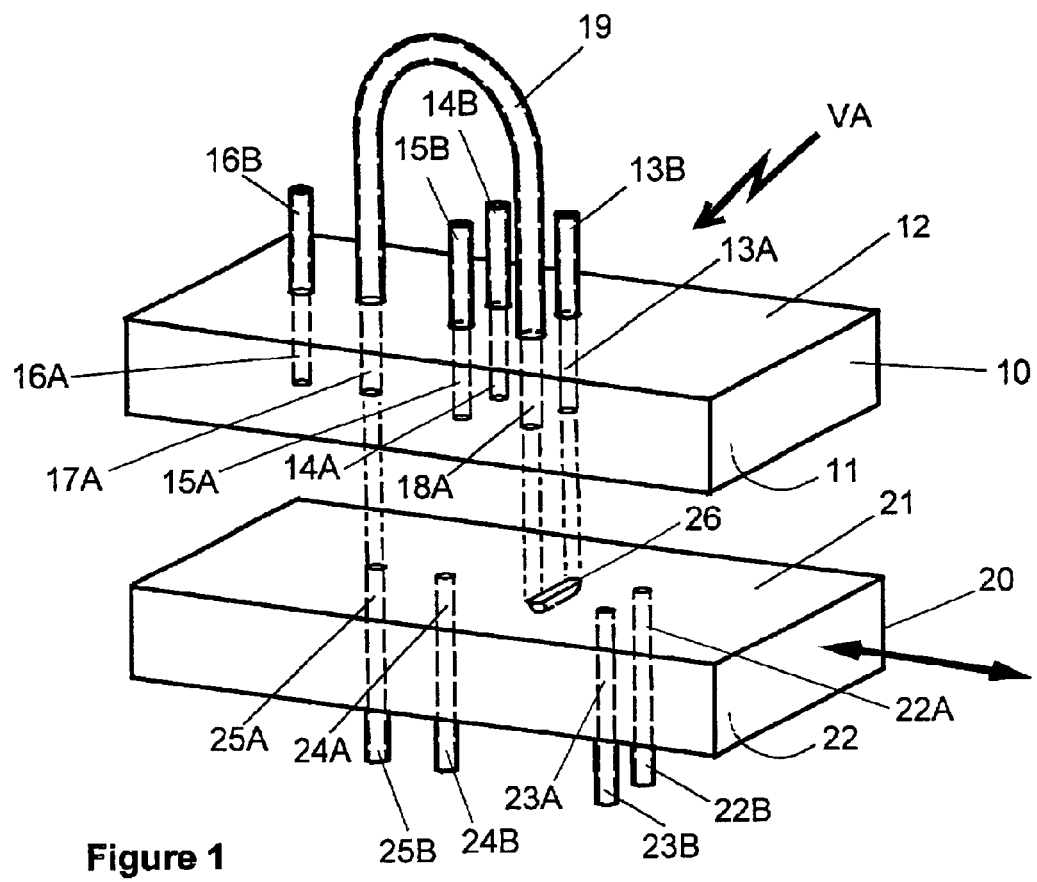
FIG. 1 is an exploded perspective illustration of a valve assembly configured in accordance with a preferred embodiment of the invention.
Figure 2:
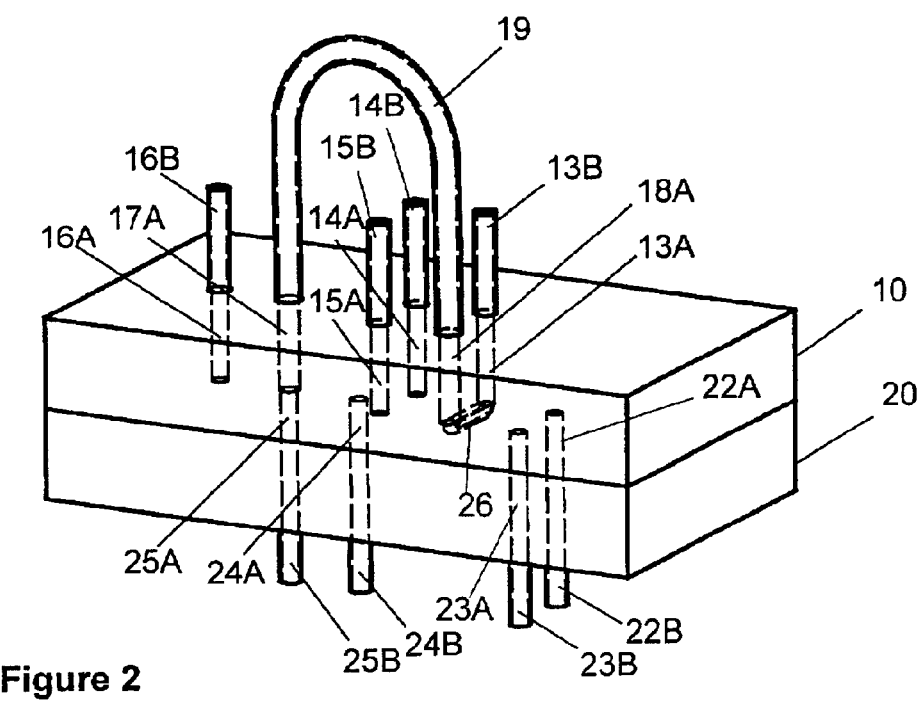
FIGS. 2 and 3 illustrate the respective positions of the two valve pads shown in FIG. 1 in liquid-loading and liquid-dispensing positions, respectively.
Figure 3:
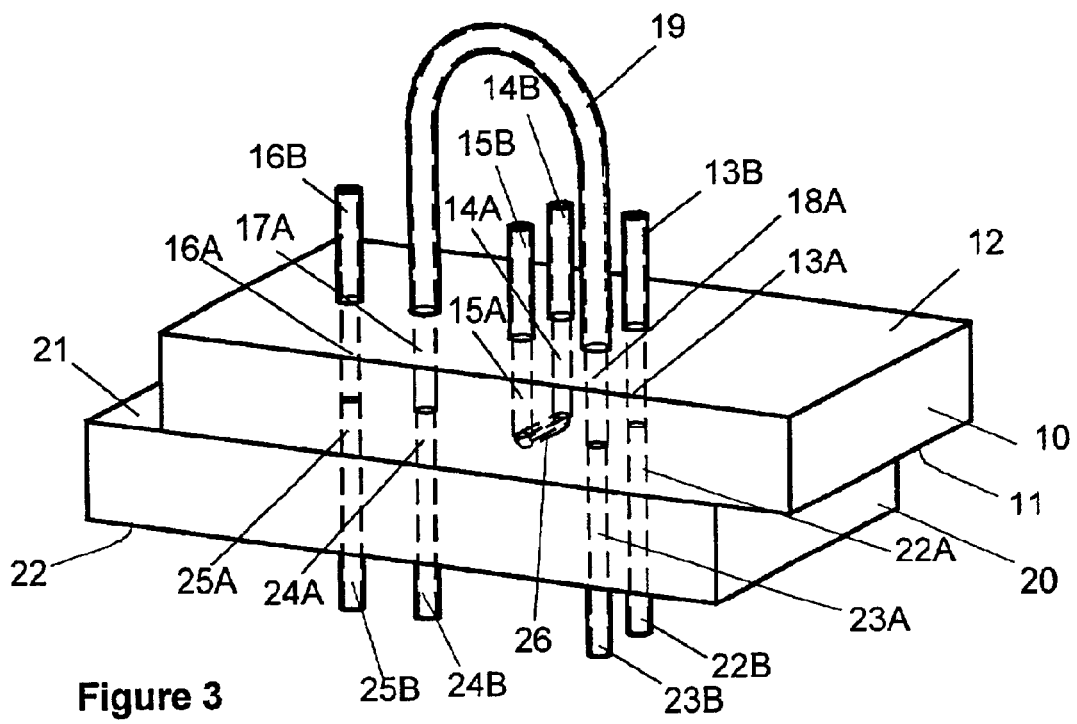

Referring now to the drawings, FIGS. 1–3 illustrate the basic details of a dual-pad shear valve assembly VA structured in accordance with a preferred embodiment of the invention. The valve assembly includes a first valve body 10, configured as a 'tile' or 'pad' of a ceramic material, plastic, stainless steel or like materials used for liquid flow control applications, and having a first, generally planar inner surface 11 (the bottom surface as viewed in FIG. 1) and a second outer surface 12 (the top surface as viewed in FIG. 1) spaced apart therefrom by the thickness of the material of the pad. Although its shape may vary, in accordance with a preferred embodiment, the outer surface 12 of the first valve pad 10 is also preferably generally flat (planar), as shown. Making the outer surface 12 of the valve pad 10 generally flat facilitates installation and retention of the valve pad 10 within the valve housing (as will be described with reference to FIG. 4).

The first valve pad 10 is also shown as containing a plurality of liquid pathways 13A, 14A, 15A, 16A, 17A, and 18A that pass perpendicularly through the pad. Preferably, each of such pathways has a circular transverse cross-section so as to define a cylindrical bore that intersects the first and second surfaces of the pad orthogonally. Four of these liquid pathways, 13A–16A, are fluidly connected to four ports, 13B–16B, respectively, such ports preferably extending normal to the second surface 12. The other two liquid pathways 17A and 18A are fluidly connected to an external hollow loop 19 that interconnects these two pathways. Preferably, loop 19 has a circular cross section and a length that, together with the volumes defined by pathways 17A and 18A, define one of two prescribed volumes of liquid to be isolated and dispensed by the valve assembly. Also, the surface 11 of valve pad 10 is preferably provided with a cleaning groove 54 (shown in FIG. 4), that is adapted to be ported, via liquid paths 55 and 56, to a vacuum source (not shown), so as to scavenge any debris that may accumulate on either of the engaging surfaces of the valve pads.

Confronting the first valve body 10 is a second valve body (tile/pad) 20 having a first generally planar inner surface 21 (its top surface as viewed in FIG. 1) and a second outer surface 22 (the bottom surface as viewed in FIG. 1) spaced apart therefrom by the thickness of the material of the valve pad 20. It is this planar inner surface 21 that engages the planar inner surface 11 of pad 10 to produce the "shearing" effect by which the different liquid pathways in the valve assembly are opened and closed to liquid flow as the pads are slid relative to each other. As in the case of 10, it is also preferred that the outer surface 22 of valve pad 20 is generally flat or planar, as shown. Configuring the outer surface 22 of the valve pad to be generally flat facilitates spring-biased retention of the pad 10 within a valve housing, shown in FIGS. 7–10, to be described.

As shown in FIGS. 1–3, the second valve pad 20 defines a plurality of liquid pathways 22A, 23A, 24A and 25A. As in the case of pad 10, each of these liquid pathways are preferably in the form of a cylindrical bore that passes completely through the pad, intersecting the opposing planar surfaces substantially orthogonally. Pathways 22A–25A are fluidly connected to ports 22B–25B, respectively, such ports preferably extending orthogonally outward from outer surface 22. A key element of valve pad 20 is the presence of an open, liquid-retaining channel 26 that is cut or otherwise formed in the planar surface 21. The dimensions of this channel are such as to define a second prescribed volume of liquid that is to be isolated and dispensed by the valve assembly of the invention.

FIGS. 2 and 3 illustrate, respectively, the relative positions of valve pads 10 and 20 when the valve assembly is operating in its liquid-loading and liquid-dispensing states. While either or both of the pads may be selectively slid in a linear direction parallel to the planar surfaces 11 and 21 for the purpose of opening and closing the aforementioned pathways and ports, in the embodiment shown, only pad 20 slides while pad 10 remains stationary. Further, it will be appreciated that, while a linearly operated shear valve is preferred, the invention has equal utility in shear valves of the rotating variety, as discussed above with reference to the prior art.

When the valve is operating in its liquid-loading state, pad 10 is in a position in which its pathways 13A and 18A are aligned with the open, liquid-retention channel 26 formed in the planar surface 21 of pad 20. In this position, pathway 17A in pad 10 is also aligned with pathway 25A of pad 20, and its associated port 25B. Thus, to load liquid into the valve assembly, liquid is pumped into either port 13B of valve pad 10, or into port 25B of valve pad 20. In the former case, the entering blood will then fill, in order, the volumes defined by pathway 13A in pad 10, the open channel 26 in pad 20, pathway 18A in pad 10, external loop 19, pathway 17A in pad 10, pathway 25A in pad 20, and port 25B of pad 20. Obviously, the filling order is reversed in the case where the liquid enters the valve assembly through port 25B. To isolate liquid in channel 26 and loop 19, pad 20 is slid linearly to the liquid-dispense position shown in FIG. 3. In doing so, it will be appreciated that the source of the liquid entering through port 13B and pathway 13A (or through port 25B and pathway 25A) will be sheared off by the opposing planar surface 11 (or 21), and the liquid-retention channel 26 of pad 20 will become aligned with pathways 14A and 15A of pad 10, and their respective ports 14B and 15B. At the same time, the external loop 19 will, via the pathways 17A and 18A with which it is fluidly connected, become aligned with pathways 24A and 23A of pad 20 and their associated ports 24B and 23B. Thus, to dispense the isolated volumes trapped in channel 26, an expelling fluid, e.g., a diluent or non-reactive fluid, is pumped into either port 14B or 15B, and the isolated liquid will be expelled from the other port. Similarly, to dispense the liquid trapped in loop 19 and it associated pathways 17A and 18A, an expelling liquid (e.g., a diluent) is pumped into either of the ports 24B or 23B, and the trapped liquid will be expelled from the other of the two ports. As noted above, it will be appreciated that, while the shear valve assembly described above operates by producing linear motion between the valve pads, the invention is not to be construed as being limited to such movement. Clearly, any relative movement of the pads will produce the same effect, assuming the liquid pathways are appropriately positioned in the pads. In the illustrated example, liquid pathways 16A and 17A of pad 10 are arranged in a linear path that is parallel to the direction of linear movement of pad 10; the same is true of pathways pairs 15A and 18A, and 14A and 13A. The spacing between such pairs of pathway is the same for all pairs. Similarly, pathways 25A and 25B are aligned with the direction of linear movement of pad 10.

Referring to FIG. 3, it will be appreciated that, as the isolated prescribed volumes of liquid are being dispensed, pathways 25A and port 25B which, during the liquid-loading operation contained the liquid being loaded, can be rinsed with a diluent or other cleansing liquid by pumping such liquid through port 16B and pathway 16A. Similarly, port 13B and pathway 13A can be rinsed by pumping a suitable rinsing liquid through port 22B and pathway 22A.

In should be noted that the present invention is not limited to using a particular number, size or configuration of the liquid-retention channel(s). One or a plurality of such channels may be provided in either or both of the valve pads and arranged to be ported to associated loading and dispensing ports in the opposite valve pad depending upon an intended application. Only a single liquid channel has been illustrated as being provided in the valve body 20 in order to reduce the complexity of the drawings and attendant description.

Figure 4:
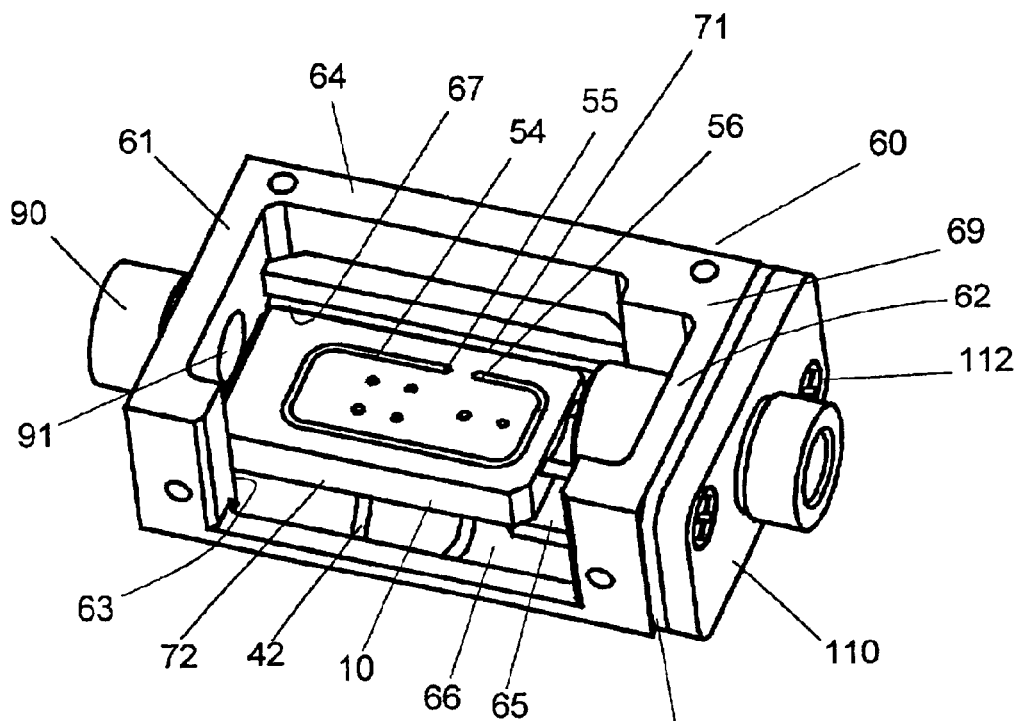
FIGS. 4 and 5 are diagrammatic front and rear perspective views of the dual pad liquid valve device of the invention showing the fixed valve pad installed in a supporting housing.
Figure 5:
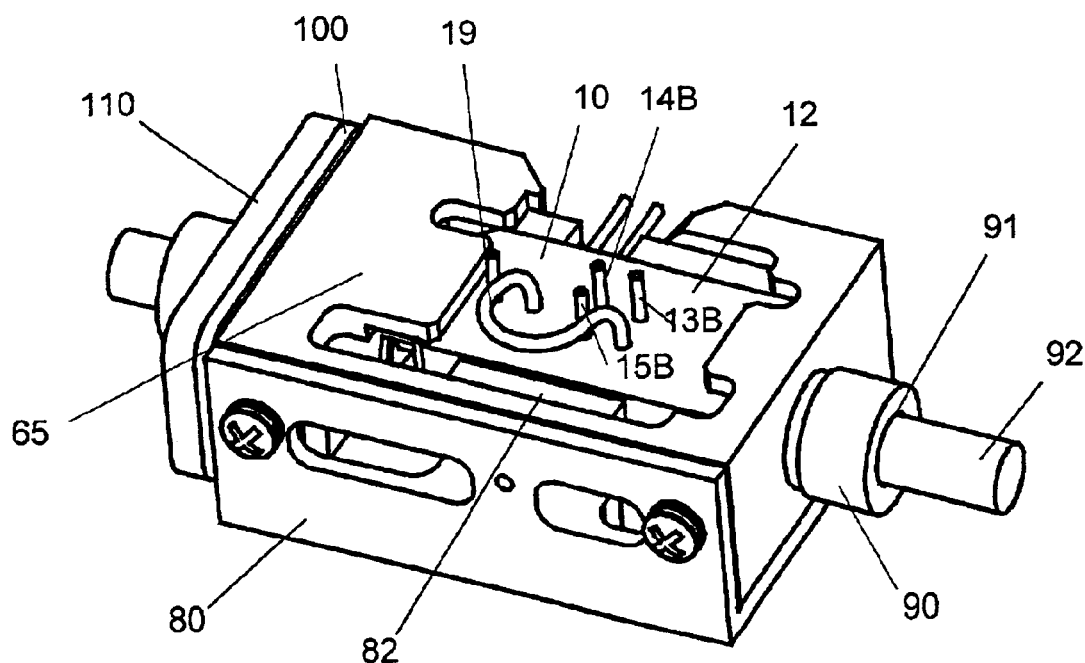

Attention is now directed to FIGS. 4–10 which show the manner in which the components of the linearly sliding, dual valve pad mechanism of FIGS. 3 and 4, described above, may be compactly supported within a common housing for relative translational movement therebetween by respective linear actuator mechanisms coupled to opposite ends of the movable valve pad 20. As shown in the perspective view of FIG. 4 and its associated obverse perspective view of FIG. 5, the valve housing comprises a generally hollow, solid rectangular block 60 having a set of mutually intersecting opposite end walls 61, 62, respective front and rear walls 63, 64, and a bottom wall or floor 65 portion that define an interior valve cavity 66.

Figure 6:
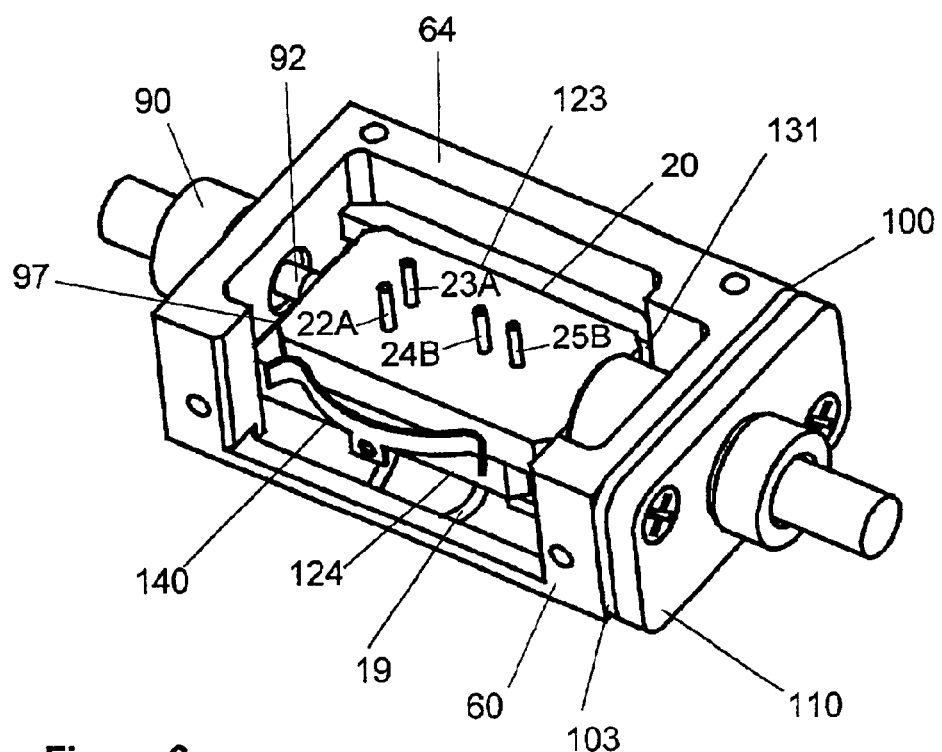
FIG. 6 is a diagrammatic perspective view of the dual pad liquid valve device of FIG. 5 showing the installation of the movable valve pad.

The body's rear wall 64 has an interior edge surface 67 that is adapted to engage a first side 71 of the first (fixed) valve pad 10, when the valve pad 10 is placed against the interior surface of the floor portion 65 of the body. As shown in FIG. 6, to avoid crimping or damage to the loop of conduit 42 which extends from the surface 12 of the valve pad 10, the conduit may be bent generally parallel with the surface 12 of the valve pad 10. Also, to enhance the fitting strength between the liquid conduits and the liquid paths of the valve pads, relatively shallow depressions may be formed in the surfaces 12 and 22 of the valve pads 10 and 20, to which the liquid conduits are ported, to allow for the addition of a strengthening adhesive, such as epoxy, and the like, at the liquid conduit to valve pad attachment locations.

A second, opposite side edge 72 of the fixed valve pad 10 is engageable by an interiorly projecting lip portion 82 of a generally L-shaped cover 80 that is attachable to the top and rear walls 64 and 69, respectively, of the housing block 60. When so attached, the interiorly projecting lip portion 82 of the L cover 80 holds the valve pad 10 against the interior edge surface 67 of the rear wall 64 of the housing block 60.

Protruding from the outer surface of the block's end wall 61 is a (generally cylindrical) mesa 90 having a bore 91 therethrough that opens into the housing's interior valve cavity 66. The bore 91 is sized to receive the drive rod 92 of a first linear actuator, shown at 93 in FIG. 9. As a non-limiting example, this and a second linear actuator shown at 96 in FIG. 9 may comprise readily commercially available components, such as pneumatic actuators, solenoid actuators, and the like. As shown in the perspective view of FIG. 6, the actuator drive rod 92 is adapted to engage an end surface 97 of the second, translatable valve pad 20.

Figure 7:
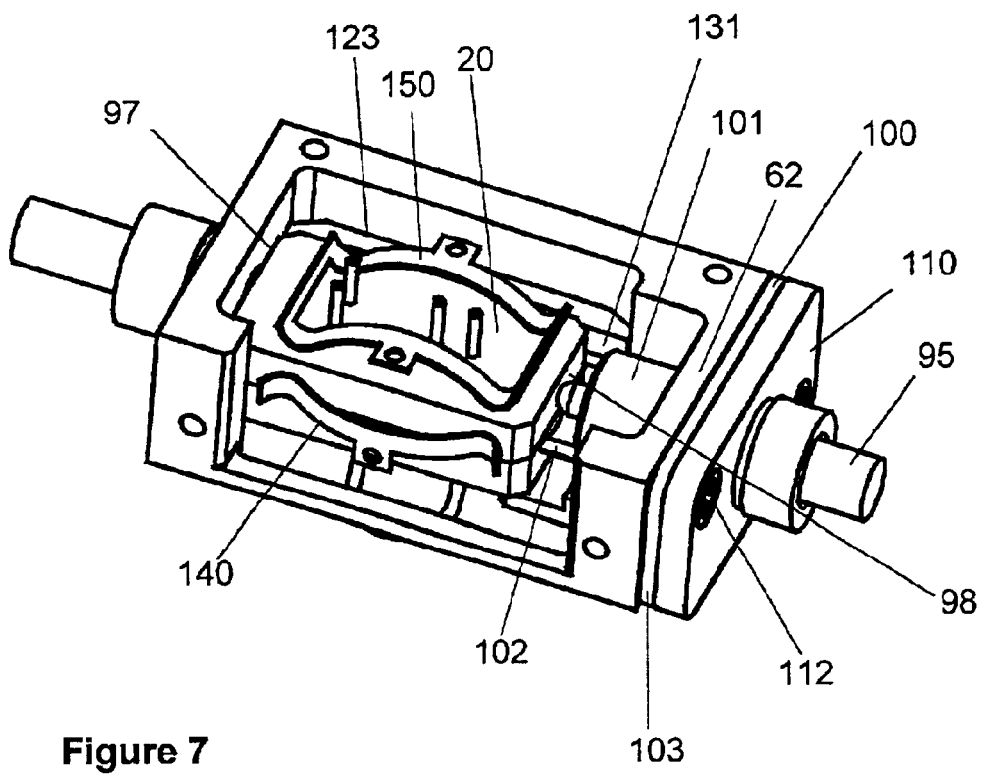
FIG. 7 is a diagrammatic perspective view of the dual pad liquid valve device of FIG. 6 showing the installation of alignment and pressure springs against the movable valve pad.

Referring to FIG. 7, the opposite end wall 62 of the support block 60 has an opening (not shown) that is sized to receive a generally cylindrical leg portion 101 of a generally 'T'-shaped end fitting 100. Leg portion 101 of the T fitting 100 includes a semi-cylindrical end portion 102, that accommodates sliding translation of the second valve pad 20 thereover. The end fitting 100 also includes an end plate portion 103 sized to engage the external surface of the end wall 62. The generally cylindrical leg portion 101 of the T fitting 100 has an axial bore that sized to receive the drive rod 95 of the second external actuator 96, shown in FIG. 9, referenced above. The second actuator's drive rod 95 is adapted to engage a second end surface 98 of the translatable valve pad 20.

The length of the leg portion 101 of the T fitting 100 is defined such that, when the end plate portion 103 is placed upon the external surface of the end wall 62, the semi-cylindrical end portion 102 engages an end wall 73 (shown in FIG. 1) of the fixed valve pad 10 that has been placed against the interior of the first end wall 61, as described above. In this manner, opposite ends 73 and 74 of the valve pad 10 are captured between the first end wall 61 and the T fitting 100.

Also, the first and second sides 71 and 72, respectively, of the fixed valve pad 10 are captured between the interior edge 67 of the block's rear wall 63 and the interior lip portion 82 of the L-shaped cover 80, as described above. The end plate portion 103 of the T fitting 100 is retained against the external surface of the block's end wall 62 by means of an actuator bracket 110 placed thereon and attached to the end wall 62 by means of suitable fittings (e.g., screws 112) that pass through bores in the T-fitting's end plate 103.

Figure 8:
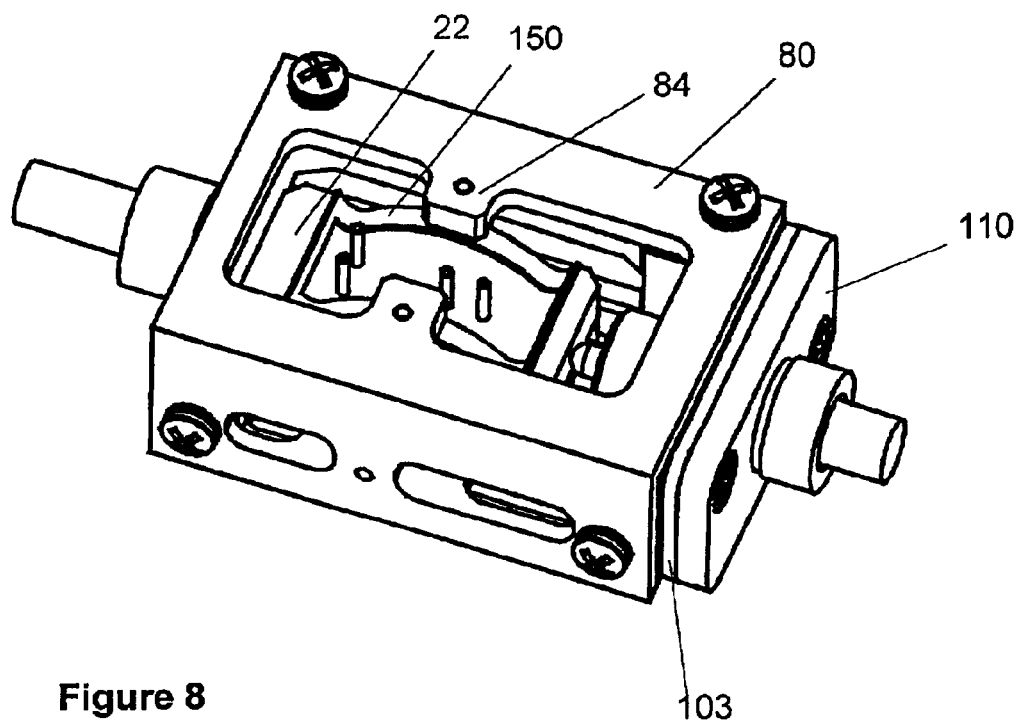
FIG. 8 is a diagrammatic perspective view of the dual pad liquid valve device of FIG. 6 showing the L-shaped cover.
Figure 9:
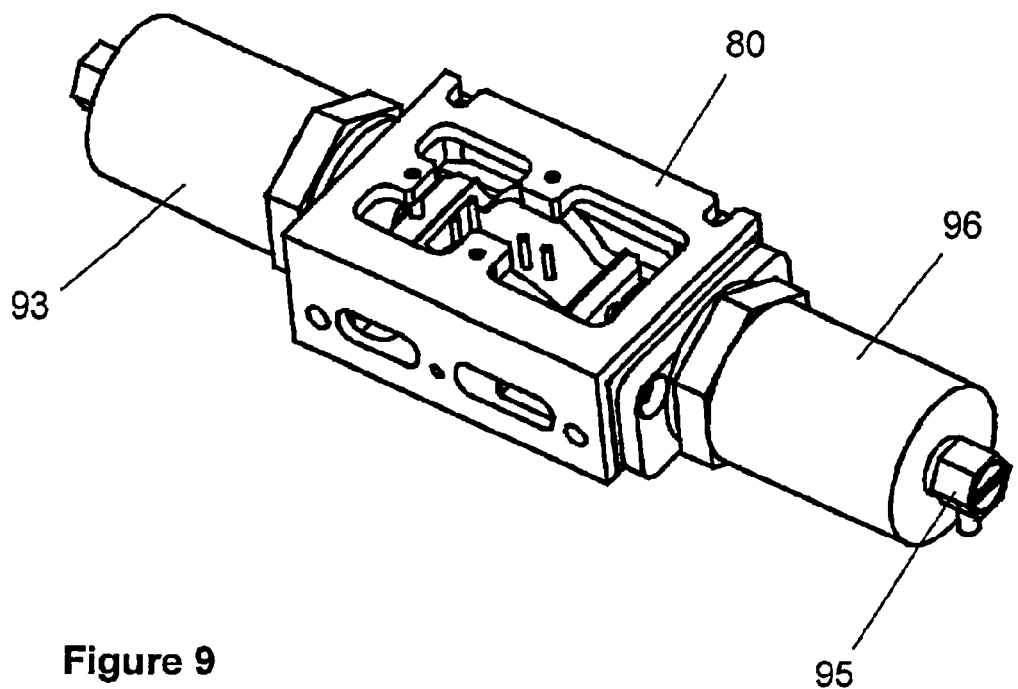
FIG. 9 is a diagrammatic perspective view of the dual pad liquid valve device of the invention showing the installation of first and second linear actuators.

As shown in FIGS. 6 and 7, the second (movable) valve pad 20 has a first side 123 urged against an interior side ledge portion 131 of the support block's rear wall 64 by an alignment biasing spring 140. The alignment spring 140 is captured between the interior surface of the L-cover 80 and a second side 124 of the moveable valve pad 20. In a similar manner, as shown in FIG. 8, a valve pad sealing pressure spring 150 is captured between the interior lip regions 84 and 85 of the cover 80 and the surface 22 of the movable valve pad 20, so that surface 21 of the movable pad 20 is urged with a prescribed sealing pressure against the opposing surface 11 of the fixed valve pad 10. To reduce wear on the spring, strips of low friction material, such as Teflon or the like, may be provided along the surface 22 of the movable valve pad 20, so that the spring slides along the low friction strips during linear translation of the movable valve pad.

Figure 10:
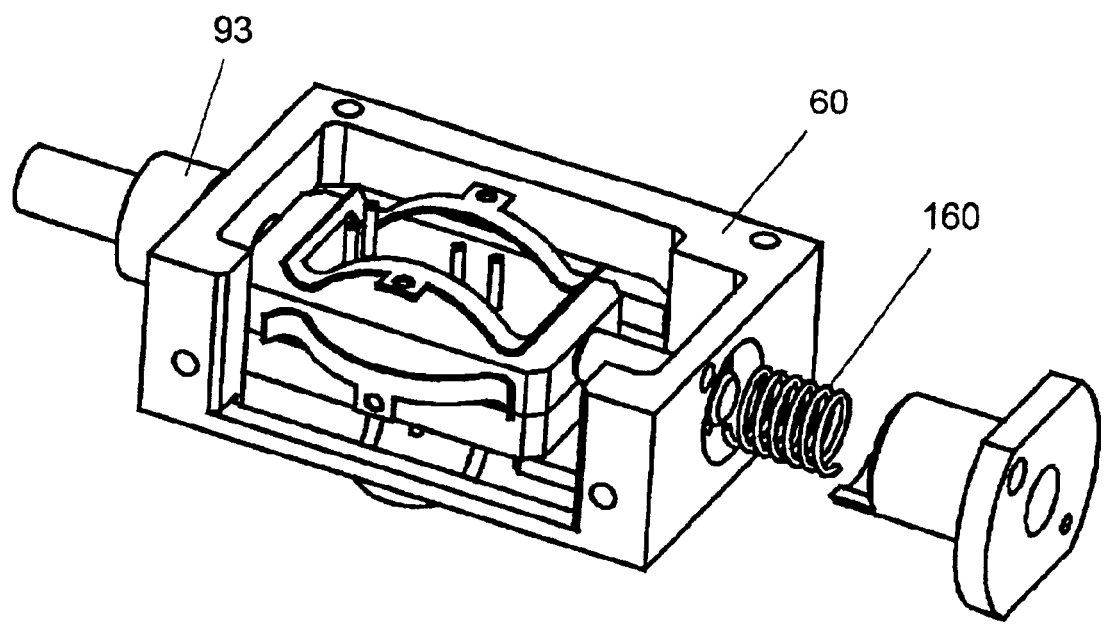
FIG. 10 shows an alternative embodiment of the dual pad liquid valve device of the invention having a movable pad return spring in place of a linear actuator.

Although the foregoing embodiment employs respective linear actuators to engage opposite ends of the movable valve pad 20, as shown in FIG. 11, one of the linear actuators (e.g., actuator 96) may be replaced by a return spring, such as the coil spring 160 in FIG. 10. In this alternative embodiment, the return spring 160 is used to bias the translatable valve pad 20 to a first, preset liquid flow position, against which the linear actuator 93 operates to displace the movable valve pad 20 to a second liquid flow position.

In operation, in response to control of the actuator(s) to place the movable valve pad in a first translational position (shown in FIG. 2), the liquid-retention channel 26 in the movable valve pad 20 becomes part aligned with liquid flow ports in the fixed pad 10 within a liquid charging path, allowing the channel 26 to be filled with charging liquid, as described above. Thereafter, as the actuator(s) are controlled to cause the movable pad 20 to be linearly displaced to a second translation position (shown in FIG. 3), the engaging surfaces 11 and 21 of the two valve pads provides for retention by the liquid-retention segment 26 of the charged liquid volume.

At the second translation position, the prescribed volume of liquid that has been captured by and retained in the liquid-retention channel 51 of the movable valve pad 20 may then be removed by porting its pair of liquid paths to a carrier transport path through the fixed valve pad 10. As pointed out above, since the volume of captured liquid is defined by the geometry of the retention channel 26 and therefore known a priori, the ratio of captured liquid to carrier volume is readily determined.

As will be appreciated from the foregoing description, the present invention effectively overcomes the noted shortcomings of conventional liquid valve structures including rotational pad configured architectures, by means of a relatively physically compact, dual pad-based valve arrangement, in which at least one of a pair of generally planar surface engaging valve pads contains one or more liquid retention channels adapted to be brought into alignment with liquid ports of the adjacent pad. This open channel architecture obviates the need for three separate pads as has been traditionally used to isolate and dispense a prescribed volume of liquid, the result being a more reliable and lower cost product.

While the invention has been described with reference to particularly preferred embodiments, it is to be understood numerous changes and modifications can be made without departing from the spirit of the invention, and such changes and modifications are intended to be encompassed by the ensuing claims.

What is claimed is:

1. A dual-pad liquid shear valve assembly for isolating a first, relatively small prescribed volume of sample liquid from a larger volume of sample liquid presented to said valve assembly from a source of sample liquid and for positioning said prescribed volume of sample liquid for subsequent dispensing together with a diluent adapted to dilute said sample liquid, said valve assembly comprising:
   a first valve pad having a first planar surface and containing a first plurality of liquid pathways therethrough which intersect said first planar surface;
   a second valve pad having a second planar surface and containing a second plurality of liquid pathways therethrough which intersect said second planar surface, said first and second planar surfaces of said first and second valve pads slidably engaging each other to enable selected ones of said first plurality of liquid pathways to be moved into and out of liquid flow alignment with selected ones of said second plurality of liquid pathways, said second planar surface having formed therein an open, liquid-retention channel having a volume equal to said prescribed volume, said open, liquid-retention channel being positioned on said second planar surface to be selectively aligned and coupled with (i) a first pair of liquid pathways of said first valve pad during relative sliding movement between said first and second planar surfaces to enable said open, liquid-retention channel to be filled with a sample liquid supplied by a sample liquid source, and (ii) a second pair of liquid pathways of said first valve pad during relative sliding movement between said first and second planar surfaces to enable said prescribed volume of sample liquid contained in said open, liquid-retention channel to be dispensed therefrom by the introduction of a diluent into one of said second pair of liquid pathways.

2. The valve assembly as defined by claim 1 further comprising an external hollow loop fluidly connected with two of said first plurality of pathways, one of said two pathways being the same as one of said first pair of pathways by which said open, liquid-retention channel is filled with liquid, whereby said hollow loop can be filled with said sample liquid in series with said open, liquid-retention channel, said external hollow loop having a prescribed volume which, when added to the volumes of said two pathways, defines a second prescribed volume of sample liquid to be isolated and dispensed by said valve assembly.

3. The valve assembly as defined by claim 2 wherein said external hollow loop is positioned to be selectively aligned and coupled with (i) said two of said first plurality of pathways of said first valve pad during relative sliding movement between said first and second planar surfaces to enable said open, liquid-retention channel to be filled with a sample liquid supplied by a sample liquid source, and (ii) a second pair of liquid pathways of said second valve pad during relative sliding movement between said first and second planar surfaces to enable said prescribed volume of sample liquid contained in said external hollow loop to be dispensed therefrom by the introduction of a second diluent into one of said second pair of liquid pathways of said second valve pad.

4. The valve assembly as defined by claim 2 wherein said external hollow loop is supported by said first valve pad.

5. The valve assembly as defined by claim 1 wherein one of said valve pads is fixed and the other is slidably mounted relative thereto.

6. The valve assembly as defined by claim 1 further comprising a drive mechanism for imparting relative sliding movement between said first and second planar surfaces of said first and second valve pads.

7. The valve assembly as defined by claim 1 further including a housing having an internal cavity configured to support said first valve pad in a fixed position therein, and also supporting said second valve pad for linearly slidable translation with respect to said first planar surface of said first valve pad, and a linear translation actuator arrangement coupled to spaced apart locations of said second valve pad, and being adapted to effect linear translation of said second valve pad with respect to said first planar surface of said first valve pad.

8. The valve assembly as defined by claim 7 wherein said first valve pad is retained in said fixed position by a first portion of said housing and a support element for said linear translation actuator arrangement.

9. The valve assembly as defined by claim 8 wherein said first valve pad is retained in said fixed position by a second portion of said housing and a cover attached to said housing.

10. The valve assembly as defined by claim 8 wherein said second valve pad is supported for pre-aligned linear slidable translation with respect to said first planar surface of said first valve pad by a mechanical biasing structure captured between said cover and said second valve pad.

11. The valve assembly as defined by claim 7 wherein said linear translation actuator arrangement includes a linear actuator supported adjacent to said first portion of said housing and a linear translation device supported adjacent to said second portion of said housing, and wherein said support element for said linear translation actuator arrangement is configured to accommodate linear translation of said second valve pad thereover.

12. The valve assembly as defined by claim 1 wherein said first planar surface of said first valve pad defines a cleaning groove adapted to be ported via a liquid pathway through said first pad to a vacuum source.

13. A dual-pad shear valve assembly for isolating and dispensing a prescribed volume of whole blood in a blood-analyzing instrument, said shear valve assembly comprising:
   a first valve pad having a first planar surface and containing a first plurality of liquid pathways therethrough which intersect said first generally planar surface; and
   a second valve pad having a second planar surface and containing a second plurality of liquid pathways therethrough which intersect said second planar surface, said second planar surface of said second valve pad slidably engaging said first planar surface of said first valve pad and being adapted to bring selected ones of said first plurality of liquid pathways into liquid flow alignment with selected ones of said second plurality of liquid pathways during sliding movement between said first and second planar surfaces, said second planar surface of said second valve pad having formed therein an open liquid-retention channel having a volume equal to said prescribed volume and being adapted to be coupled with liquid pathways of said first plurality of liquid pathways of said first valve pad, and wherein said first and second valve pads are adapted to be translated relative to one another so as to isolate said open liquid-retention channel of said second valve pad from liquid pathways of said first plurality of liquid pathways of said first valve pad.

14. The valve assembly as defined by claim 13 wherein said first and second valve pads are mounted for relative linear sliding movement.

15. The valve assembly as defined by claim 13 wherein one of said valve pads is supported in a fixed position and the other valve pad is mounted for linear sliding movement relative to said one valve pad.

16. The valve assembly as defined by claim 13 further comprising an external hollow loop fluidly connected with two of said first plurality of pathways, one of said two pathways being used to fill said open liquid-retention channel with whole blood, whereby said hollow loop can be filled with whole blood in series with said open, liquid-retention channel.

17. The valve assembly as defined by claim 16 wherein said external hollow loop has a prescribed volume which, when added to the volumes of said two pathways, defines a second prescribed volume of liquid to be isolated and dispensed by said valve assembly.

18. The valve assembly as defined by claim 16 wherein said external hollow loop is supported by said first valve pad.

* * * * *